| United States Patent [19] | [11] | 4,126,615 |
|---|---|---|
| Turcsan et al. | [45] | Nov. 21, 1978 |

[54] PROCESS FOR THE MANUFACTURE OF PURE ISOQUINOLINE DERIVATIVES

[75] Inventors: István Turcsán; István Jelinek; József Ugrics; István Csik; Éva Somfai; Irén Császár née Tóth, all of Budapest, Hungary

[73] Assignee: Chinoin Gyogyszer es Vegyeszeti Termekek Gyara RT, Budapest, Hungary

[21] Appl. No.: 748,221

[22] Filed: Dec. 7, 1976

[30] Foreign Application Priority Data

Dec. 12, 1975 [HU] Hungary ............................ CI 1628
Dec. 12, 1975 [HU] Hungary ............................ CI 1629

[51] Int. Cl.² .......................................... C07D 217/20
[52] U.S. Cl. .................................. 542/449; 546/144; 260/465 F; 260/570.8 R

[58] Field of Search ............. 260/285, 283 SY, 289 A, 260/289 D, 570.8 R

[56] References Cited

U.S. PATENT DOCUMENTS 3,052,682  9/1962  Frommel ........................ 260/289 A Primary Examiner—Paul M. Coughlan, Jr.
Attorney, Agent, or Firm—Karl F. Ross

[57] ABSTRACT

In the production of perparine or papaverine and their hydrochlorides, the formation of impurities in the reaction mixture is suppressed by fractionating a 3,4-di-R-benzyl-cyanide in the presence of an organic base (e.g. pyridine, dimethylformamide, ethylenediamine or triethylamine) followed by hydrogenation with a Raney-nickel catalyst treated with aqueous ammonium carbonate solution. R is methoxy or ethoxy.

4 Claims, No Drawings

PROCESS FOR THE MANUFACTURE OF PURE ISOQUINOLINE DERIVATIVES

This invention relates to the manufacture of pure isoquinoline derivatives and salts thereof.

It is known that isoquinoline derivatives are useful spasmolytics. The 6,7,3',4'-tetraethoxy-1-benzal-1,2,3,4-tetrahydro-isoquinoline (perperine HCl), HCl 6,7,3',4'-tetraethoxy-1-benzyl-isoquinoline and 6,7,3',4'-tetramethoxy-1-benzyl-isoquinoline (papaverine) and its hydrochlorides are particularly potent spasmolytics.

The first synthesis of 6,7,3',4'-tetramethoxy-1-benzyl-isoquinoline (referred to below as Papaverin) feasible on industrial scale was described in Hungarian Patent No. 108,865.

According to the most uptodate procedures a dialkoxybenzene is subjected to chloromethylation, the 1,2-dialkoxy-4-chloromethyl-benzene thus obtained is reacted with an alkali metal cyanide, the 3,4-dialkoxy-benzyl cyanide thus obtained is subjected to fractionation and thereafter to hydrogenation in the presence of ethanol and a Raney-nickel catalyst, the 1,2-dialkoxy-4-amino-ethyl-benzene is reacted with 3,4-dialkoxy-phenyl-acetic acid, the N-(3',4'-dialkoxyphenyl-acetyl)-3,4-dialkoxy-phenyl-ethylamine is subjected to ring-closure in the presence of phosphorous oxychloride and the isoquininone derivative of the formula IA

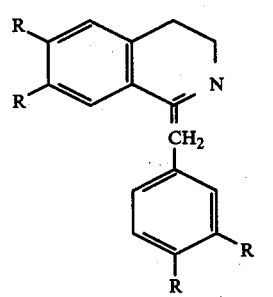

or IC

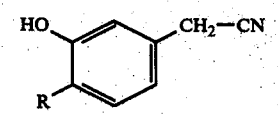

is optionally dehydrogenated in the presence of a Raney-nickel catalyst (Hungarian Pat. Nos. 149,740, 150,535, 150,372, 156,817 and 155,539; Chemie Industrie 92, /1964/232).

The present invention is directed to a process for the manufacture of isoquinoline derivatives of the formulae IA

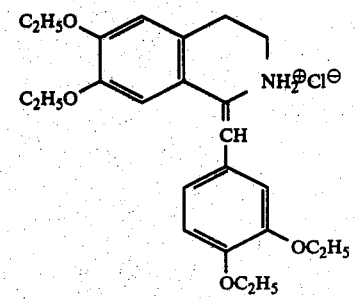

and IB

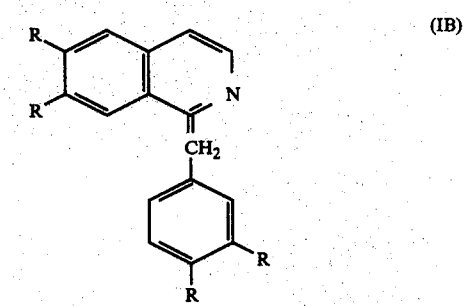

(wherein R is methoxy or ethoxy) and salts thereof by chloromethylating a di-benzene, reacting the 1,2-di-R-4-chloromethyl-benzene thus obtained with an alkali metal cyanide, thereafter hydrogenating the product obtained in the presence of ethanol and Raney-nickel catalyst, reacting the 3,4-di-R-phenyl-ethyl-amine thus obtained with 3,4-di-R-phenyl-acetic acid, cyclising the N-(3',4'-di-R-phenyl-acetyl)-3,4-di-R-phenyl-ethylamine in the presence of phosphorous oxychloride and if desired dehydrogenating the base of the isoquinoline derivative thus obtained in the presence of a Raney-nickel catalyst. According to the invention the formation is suppressed of the compounds of the formulae II, III, IV, V and VI

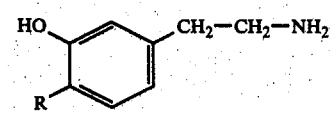

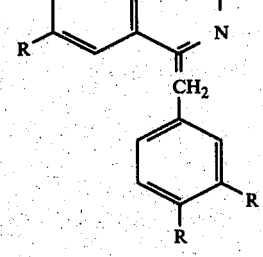

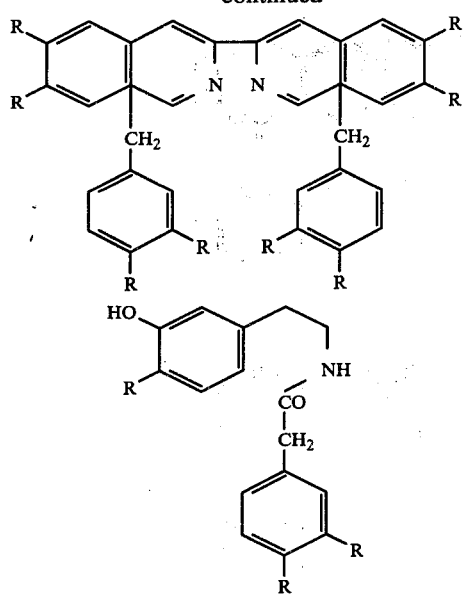

by fractionating a 3,4-di-R-benzyl cyanide in the presence of an organic base and thereafter hydrogenating in the presence of a Raney-nickel catalyst, which was previously made free of sodium hydroxide with aqueous extraction and treated with ammonium carbonate (wherein R has the same meaning as stated above).

According to a preferred embodiment of the present invention fractionation of the 3,4-di-R-benzyl cyanide is carried out in the presence of pyridine, dimethylformamide, ethylenediamine or a trialkylamine, preferably triethylamine.

For the hydrogenation step it is preferable to use a Raney-nickel catalyst, which has been previously treated with a 3% aqueous ammonium carbonate solution.

The treatment of the catalyst with ammonium carbonate is a critical feature of our invention. One may proceed preferably by using for the reduction a Raney-nickel catalyst previously treated with a 3% aqueous ammonium carbonate solution and/or adding to the reaction mixture in the course of reduction 1-1.5% by weight of ammonium carbonate calculated on the substrate.

The present invention is based on the recognition that when carrying out the above reaction sequence in the "acid amide" phase of the synthesis hitherto unknown impurities are formed which can not be detected at all or only with great difficulty according to the conventional analysis methods.

It has been found on the basis of various experiments for the determination of the structure (preparative thin layer chromatography, purification by column chromatography, mass spectrum, IR-spectrum, NMR-spectrum, structure verifying synthesis), that the impurities correspond to the general formula VI (wherein R is methoxy or ethoxy).

The acid amide derivatives of the formula VI are new compounds never described in prior art.

On studying the formation of these compounds it has been found that the mono-desalkylation leading to this structure does not take place or but to a very small extent in the "acid amide" phase but it occurs during the preceeding steps of the synthesis.

For theoretical considerations the reaction conditions used by the chloromethylation of dialkoxybenzene, subsequent $S_N2$ type nitrile formation of 3,4-dialkoxy-benzyl cyanide and subsequent catalytic hydrogenation to yield 3,4-dialkoxy-beta-phenyl-ethylamine are studied.

It is known that 1,2-dialkoxy-benzenes may be very easily chloromethylated due to the strong +T-effect of the alkoxy groups and therefore the bis- and poly-chloromethylation of the molecule can taken place even when carrying out the reaction under most careful working conditions (Hungarian Patent 156,817; Izveszt. Akad. Nauk. Arm. SzSzSzR. Szer. Him. Nauk 10, (1957) 203; Zs. Obscs. Him. 29, (1959) 3746).

For sterical and inductive reasons the by-product 1,2-dialkoxy-3,4-bis-chloromethyl-benzene can not be or can be only partly converted into the corresponding nitrile in the $S_N2$ type nitrile-forming reaction following the chloromethylation step.

Therefore the reaction mixture always contains a considerable amount of a by-product containing free chloromethyl groups. In the course of the purification steps under the extreme conditions of the vacuum fractionation at high temperature these compounds release free hydrochloric acid as a result of the known polycondensation side-reactions (Melnyikov, N.N. et al.; Zs. Obscs. Him. 29 (1959)3746). The free hydrochloric acid induces at the moment of its formation a proton catalysed thermal desalkylation. The substituted benzyl cyanide derivatives containing free phenolic hydroxy groups form partly tarry products in further polycondensation side reactions or partly contaminate the product thus decreasing the overall yield of the reaction and the purity of the product. On the basis of the above recognition we take preventive measures to inhibit the formation of these by-products.

It has been found that the non-desired desalkylation may be suppressed by binding the corresponding bis-chloromethyl compound or the hydrochloric acid formed therefrom with an equivalent amount of an organic base (triethylamine, pyridine, ethylenediamine, etc.) in the course of the purification of the product during the evaporation step or - preferably - before the vacuum fractionation.

By proceeding as stated above 3,4-dimethoxy-benzyl cyanide and 3,4-diethoxy-benzyl cyanide respectively can be prepared with a yield of 55-65% and in excellent purity and this constitutes a significant advance over hitherto known methods.

It is known that in the catalytic reduction of acid nitriles into the corresponding primary amines, the formation of secondary amines may be suppressed by using as solvent alcohol saturated with ammonia and as catalyst a Raney-nickel catalyst.

It has been found surprisingly that when reducing 3,4-dialkoxy-benzene-cyanides in the strongly basic medium with a Raney-nickel catalyst, the absorbed free alkali-content of the catalyst induces a catalytic desalkylation. This non-desired side reaction reduces the yields and influences the quality of the product in an unfavorable manner.

It has been found further that the said non-desired desalkylation may be suppressed by previously treating the catalyst with water and a 3% aqueous ammonium carbonate solution and, if desired, adding to the reaction mixture a further amount of ammonium carbonate (1-1,5% by weight related to the substrate) for further buffering.

On carrying out the process as described under paragraphs 1) and 2) by suppressing the formation of the mono-desalkylated impurities - which are extremely difficult to detect - during the preparation of the substituted benzyl cyanides and substituted phenyl-ethyl-amines, the amount of the acid amide type impurities of the formula VI (wherein R is as stated above) is significantly decreased too; the impurities of the formula VI can be readily detected; thus the isoquinoline derivatives obtained by the further steps of the synthesis (Bischler-Napieralski type ring-closure and optional catalytic dehydrogenation of the dihydroisoquinoline derivatives) can be prepared with higher yields and in purer form as compared to the hitherto known methods.

Such a great improvement of the quality of the product is particularly surprising and unaforeseen in the synthesis of 6,7,3',4'-tetraethoxy-1-benzyl-isoquinoline (Perparine) and 6,7,3',4'-tetramethoxy-1-benzyl-isoquinoline (Papaverine). The improved quality can not be simply explained with the mere elimination of the contaminations i.e., with the fact that these by-products do not primarily contaminate the end-product. Further investigations were directed to the clarification of the question.

The impurities of Papaverine and Perparine and the suitable purification methods are discussed in a great number of publications (e.g. U.S. Pat. No. 2,507,135). Particular stress is laid on the elimination of the impurities formed under oxydative effects (papaverinol, perparinol), since these contaminations make the end-product unacceptable for pharmaceutical use even if present in an amount of $10^{-4}$ % (Prod. Pharm. V. /1950/ 520).

A criterion of very great importance in the production of Papaverine and perparine meeting the requirements of Pharmacopeia is the suitable color of the product. Several authors (Hungarian Pat. No. 148,496) mention in the disclosure of the complicated purification methods the characteristic greenish-yellow shade of Papaverine-hydrochloride caused by an unknown impurity. Most pharmacopeia classify this shade as unacceptable. We have succeeded in isolating (preparative thin layer chromatography, purification by column chromatography) this impurity of Papaverine hydrochloride.

Investigations for determining the structure of this impurity have shown that this compound corresponds to the formula V (wherein R stands for methoxy or ethoxy).

The profound study of the catalytic dehydrogenation reactions has shown a correlation between the formation of the mono-desalkylated impurities containing free active phenolic hydroxy group (VI) and that of the non-desired contamination causing the discoloration (formula V).

We have stated that the dihydro-isoquinoline derivative formed from the compound of the formula VI when getting into the reaction mixture of the dehydrogenation step partially poisons the Raney-nickel catalyst. Therefore in order to achieve a suitable conversion the catalyst is to be added in a considerable excess. The increased amount of the catalyst favours on the other hand the formation of the dimer of the formula V, i.e., the homolytic cleavage and the dimerization due to the recombination of the free radicals thus formed leading to the formation of the structure of the formula V take place more easily.

The compound of the formula V (R stands for a methoxy group; Papaverine-dimer) is a new compound never described in the literature. Molecular weight 676; m.p.: 265°–268° C. In the free base form it is a white amorphous powder, the hydrochloric acid salt is of a yellow-green color. This compound changes the snow-white color of Papaverine hydrochloride when already present in an extremely small concentration. The compounds of the formula V (wherein R is ethoxy) results similarly unfavourable changes in the colour of perparine.

The removal of the said impurities from the contaminated product is almost impossible. It is a great advantage of the present invention that the formation of the said impurity is substantially suppressed by a preventive measure so that the amount of the Raney-nickel catalyst used by dehydrogenation can be decreased to one-third of the amount applied by prior art methods (Hungarian Pat. No. 150,372; C.A. 53, (1958) 17162).

In the preparation of Papaverine R is methoxy. When the preparation of perparine and 6,7,3',4'-tetraethoxy-1-benzal-1,2,3,4-tetrahydro-isoquinoline (compound of the formula IA) is concerned, R stands for an ethoxy group. This relates to the formulae IA, IB and II to VI.

Further details of the present invention are to be found in the Examples without limiting the scope of our invention to the Examples.

EXAMPLE 1

180 kg. of 1,2-dimethoxy-benzene are chloromethylated with 44 kg. of paraformaldehyde and 280 kg. of concentrated hydrochloric acid at 48°–70° C in benzene as medium. The benzene solution of the 1,2-dimethoxy-4-chloromethyl-benzene thus obtained is heated with an aqueous solution of 105 kg. of sodium cyanide in the presence of fatty alcohol sulfonate emulsifier, under stirring. After removing the solvent 200–210 kg. of crude 3,4-dimethoxy-benzene cyanide are obtained, which may be purified by means of fractionating in vacuo in the presence of 3–5 kg. of triethylamine. At 110° to 168° C per 20 Hgmm (vapour temperature) 54–58 kg. of a forerun whereafter at 168°–196° C/5–8 Hgmm. 102–106 kg. of 3,4-dimethoxy-benzylcyanide as main fraction are obtained. The forerun contains predominantly 1,2-dimethoxy-benzene- and a small amount of 3,4-dimethoxy-benzyl cyanide.

From the forerun 52 kg. of 1,2-dimethoxy-benzene are recovered. From the main fraction 85 kg. of snow-white crystalline 3,4-dimethoxy-benzyl cyanide are obtained by crystallization from ethanol. Mp.: 66°–67° C; purity: 97–99% based on the nitrogen content; according to thin layer chromatography the product is uniform. The mono-demethylated benzyl cyanide impurity is present at most in traces in such a small amount, which can not be detected by thin layer chromatography.

EXAMPLE 2

360 kg. of crystalline 3,4-dimethoxy-benzyl cyanide are heated with a 10% aqueous sodium hydroxide solution of technical purity for 16 hours to boiling. The reaction mixture is extracted with benzene, clarified with activated charcoal and the 3,4-dimethoxy-phenyl-acetic acid is precipitated from the aqueous filtrate. Thus 370 kg. of 3,4-dimethoxy-phenyl-acetic acid are obtained, which proved to be uniform by thin layer chromatography. Mp.: 98° to 100° C.

EXAMPLE 3

50 kg. of a Raney-nickel catalyst are extracted with 300 l. of water under vigorous intermittent stirring. After removal of the aqueous extract the catalyst is stirred with 100 kg. of a 3% aqueous ammonium carbonate solution vigorously for an hour. The thus treated catalyst is allowed to stand until it is used. The pretreated catalyst is dehydrated (dried) immediately before use to the necessary extent.

EXAMPLE 4

100 kg. of crystalline 3,4-dimethoxy-benzyl cyanide are hydrogenated in 310 l. of a 80 to 96% aqueous ethanol containing 9 to 12% of ammonia in the presence of 24 kg. of Raney-nickel catalyst pre-treated as described in Example 3 at 48°–60° C under a hydrogen overpressure of 8 to 10 atm. The catalyst is filtered off, the filtrate is evaporated and the residue is subjected to fractionation in vacuo. Thus 95,5 kg. of highly pure 3,4-dimethoxy-beta-phenyl-ethylamine are obtained, purity: nearly 100%. The mono-demethylated beta-phenyl-ethylamine derivative impurity is present at most in traces in such a small amount, which can not be detected by thin layer chromatography.

EXAMPLE 5

110 kg. of 3,4-dimethoxy-beta-phenyl-ethylamine and 120 kg. of 3,4-dimethoxy-phenyl-acetic acid are melt by heating to 100° to 110° C. The pH of the melt is adjusted to an approximately neutral value to methyl orange indicator, if necessary by adding 3,4-dimethoxy-beta-phenyl-ethylamine or 3,4-dimethoxy-phenyl-acetic acid respectively. The reaction mixture is stirred at 170° C for a further interval of 2 hours, whereupon the homogenous melt containing predominantly N-(3',4'-dimethoxy-phenyl-acetyl)-3,4-dimethoxy-phenyl-ethylamine is poured into a mixture of 265 kg. of benzene and 110 kg. of phosphorous oxychloride whereafter the reaction mixture is refluxed for 2 hours. After removing the solvent the excess of phosphorous oxychloride is decomposed by addition of 450 l. of anhydrous ethanol. The mixture is allowed to stand for 8 hours under cooling, whereafter the precipitated crystalline 6,7,3',4'-tetramethoxy-1-benzyl-dihydro-isoquinoline-hydrochloride is filtered off and washed with anhydrous ethanol. Thus 250 to 260 kg. of a product having an average moisture content of 8 to 15% are obtained, which is used to further steps without drying.

EXAMPLE 6

270 kg. of 6,7,3',4'-tetramethoxy-1-benzyl-dihydro-isoquinoline-hydrochloride (average moisture content: 8 to 15%) are dissolved in 600 l. of hot water, the solution is made alkaline to phenolphthaleine indicator by adding a concentrated aqueous solution of sodium hydroxide of technical purity, the precipitated 6,7,3',4'-tetramethoxy-1-benzyl-dihydro-isoquinoline base is filtered off, and washed carefully free of sodium hydroxide. The moist product is dissolved in 330 kg. of tetraline and dehydrogenated at 175° C in the presence of 12 kg. of a Raney-nickel catalyst.

After the completion of the dehydrogenation the tetraline reaction mixture is filtered from over the Raney-nickel catalyst directly into a mixture of an aqueous hydrochloric acid solution and methanol. The precipitated product is filtered off and, if necessary, recrystallized from aqueous ethanol under an inert gas atmosphere. Thus 185 kg. of snow-white 6,7,3',4'-tetramethoxy-1-benzyl-isoquinoline-hydrochloride are obtained. The product fully complies with the requirements of pharmacopeia.

EXAMPLE 7

166 kg. of 1,2-diethoxy-benzene are chloromethylated with 45 kg. of paraformaldehyde and 270 kg. of an aqueous concentrated hydrochloric acid solution at 20° to 58° C in benzene as medium. The benzene solution of the 1,2-diethoxy-4-chloromethyl-benzene thus obtained is reacted with an aqueous solution of 100 kg. of sodium cyanide in the presence of dimethylformamide under stirring and heating. After removing the solvent 180 kg. of crude 3,4-diethoxy-benzyl cyanide are obtained, which are subjected to fractionation in vacuo in the presence of 3 kg. of triethylamine. At 110° to 168° C/20 Hgmm (vapour temperature) 46 kg. of a forerun, whereafter at 168° to 196° C/5 to 8 Hgmm (vapour temperature) 112 kg. of 3,4 -diethoxy-benzyl cyanide as main fraction are obtained. The forerun contains predominantly 1,2-diethoxy-benzene and a small amount of 3,4-diethoxy-benzyl cyanide. From the forerun 41 kg. of 1,2-diethoxy-benzene are recovered. The main fraction is again subjected to fractionation in vacuo to yield 94 kg. of 1,2-diethoxy-benzyl cyanide. The purity of the product amounts to 97 to 99% based on the nitrogen content. According to thin layer chromatography the product is substantially uniform. Mono-deethylated benzyl cyanide derivative impurity is present at most in traces in such a small amount, which can not be detected by means of thin layer chromatography.

EXAMPLE 8

360 kg. of 3,4-diethoxy-benzyl cyanide are heated with 1800 kg. of a 10% sodium hydroxide solution of technical quality for 40 hours to boiling. The reaction mixture is extracted with benzene, whereupon the 3,4-diethoxy-phenyl-acetic acid is precipitated by acidifying the saturated aqueous solution. Thus 370 kg. of 3,4-diethoxy-phenyl-acetic acid are obtained, the product melts at 79°–81° C and is uniform as determined by thin layer chromatography.

EXAMPLE 9

100 kg. of 3,4-diethoxy-benzyl cyanide are hydrogenated in 310 l. of a 80 to 96% aqueous ethanol containing 9 to 12% of ammonia in the presence of 24 kg. of a Raney-nickel catalyst pretreated according to Example 3, at 45° to 68° C under a hydrogen overpressure of 8 to 10 atm. The catalyst is filtered off, the solution is evaporated and the residue is subjected to fractionation in vacuo. Thus 96 kg. of highly pure 3,4-diethoxy-beta-phenyl-ethylamine are obtained. The purity is almost 100%. The mono-desethylated beta-phenyl-ethylamine derivative is present at most in traces in such a small amount, which can not be detected by thin layer chromatography.

EXAMPLE 10

100 kg. of 3,4-diethoxy-beta-phenyl-ethylamine and 110 kg. of 3,4-diethoxy-phenyl-acetic acid are melt by heating to 100° to 110° C. The pH of the melt is adjusted to an approximately neutral value to methyl orange indicator if necessary by adding 3,4-diethoxy-beta-phenyl-ethylamine, or 3,4-diethoxy-phenyl-acetic acid respectively. The reaction mixture is stirred at 170° C for a further 2 hours, whereafter the homogenous melt containing predominantly N-(3',4'-diethoxy-phenyl-acetyl)-3,4-diethoxy-phenyl-ethylamine is poured into a mixture of 280 kg. of benzene and 100 kg. of phosphorous oxychloride, whereupon it is refluxed for 2 hours. After removing the solvent the excess of phosphorous oxychloride is decomposed by adding 400 l. of anhydrous ethanol. The mixture is allowed to stand under cooling for 8 hours, whereupon the precipitated crystalline 6,7,3',4'-tetraethoxy-1-benzal-1,2,3,4-tetrahydro-isoquinoline-hydrochloride is filtered off and washed with anhydrous ethanol. The moist product may be recrystallized from ethanol if necessary. Thus 183 kg. of 6,7,3',4'-tetraethoxy-1-benzal-1,2,3,4-tetrahydro-isoquinoline-hydrochloride are obtained.

EXAMPLE 11

175 kg. of 6,7,3',4'-tetraethoxy-1-benzal-1,2,3,4-tetrahydro-isoquinoline-hydrochloride are dissolved in 600 l. of hot water, whereupon the solution is made alkaline to phenolphthaleine indicator by adding a concentrated aqueous sodium hydroxide solution of technical purity. The quinoline base thus obtained is filtered off, washed carefully free of sodium hydroxide and the moist product is dissolved in 250 of tetraline. The product is dehydrogenated in the presence of 14 kg. of a Raney-nickel catalyst at 172° to 175° C.

After the completion of the dehydrogenation reaction the tetraline reaction mixture is filtered from over the Raney-nickel catalyst directly into a mixture of aqueous hydrochloric acid and isopropanol. The immediately precipitated 6,7,3',4'-tetraethoxy-1-benzyl-isoquinoline-hydrochloride is filtered off and, if necessary, recrystallized from aqueous ethanol under inert gas atmosphere. Thus 135 kg. of snow-white perparine hydrochloride are obtained, which complies with the requirements of pharmacopeia.

The spectral data of the acylamide type impurity of the formula VI (R is methoxy) are as follows:
Mass spectrophotometrical analysis:
Measuring place: Structure investigating laboratory of the Hungarian Academy of Sciences.
Apparatus: MS-902; induction 70.000 V; direct addition.
On the basis of the mass spectrum the molecular weight amounts to 345; empirical formula $C_{19}H_{23}NO_5$.
The fragments are split off in the following order:
1. $C_9H_{10}O_2$
2. $CONH_2$
3. residual part $C_9H_9O_2$.

Demethylation in position 3 is verified by several preliminary model experiments:

| IR spectrum | |
|---|---|
| $\gamma$ C=O "amide I band" | 1655 cm$^{-1}$ |
| $\delta$ NH "amide II band" | 1530 cm$^{-1}$ |
| $\gamma$ crystal water | 3350 cm$^{-1}$ |
| $\delta$ H—O—H— | 1615 cm$^{-1}$ |

The mass spectrophotometrical analysis of the compound of the formula V (R=methoxy) is as follows:
Measuring place: Structure investigating laboratory of the Hungarian Academy of Sciences.
Apparatus: MS-902; induction 70.000 V; direct addition.
Molecular weight: 676,283
In view of the measuring errors the most probable empirical formula is $C_{40}H_{40}N_2O_8$

What we claim is:

1. In a process for the manufacture of isoquinoline derivatives of the formulae IA and IB

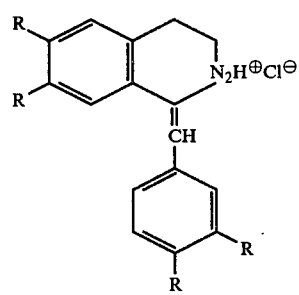

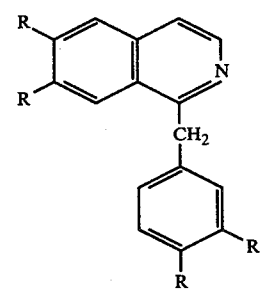

wherein R is methoxy or ethoxy, by steps which include chloromethylating a di-R-benzene, reacting the 1,2-di-R-4-chloromethyl-benzene thus obtained with an alkali metal cyanide, thereafter hydrogenating the product obtained in the presence of ethanol and a Raney-nickel catalyst, reacting the 3,4-di-R-phenyl-ethylamine thus obtained with 3,4-di-R-phenyl-acetic acid, and cyclizing the N-(3',4'-di-R-phenyl-acetyl)-3,4-di-R-phenyl-ethylamine in the presence of phosphorous oxychloride, the improvement which comprises suppressing the formation of the compounds of the formulae II, III, IV, and VI

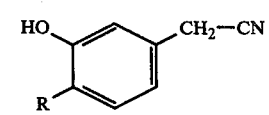

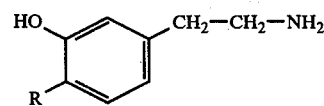

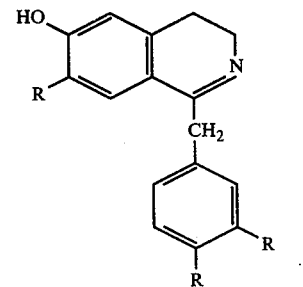

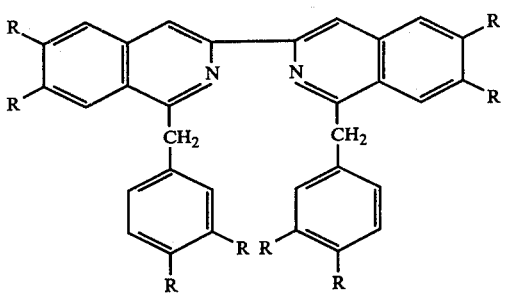

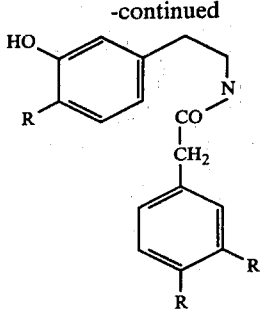

by fractionating a 3,4-di-R-benzyl-cyanide in the presence of an acid-binding organic base and thereafter hydrogenating the 3,4-di-R-benzyl-cyanide in the presence of a Raney-nickel catalyst, which was previously made free of sodium hydroxide with aqueous extraction and treated with ammonium carbonate.

2. The improvement defined in claim 1 wherein the fractionation is effected in the presence of pyridine, dimethyl- formamide, ethylenediamine or triethylamine.

3. The improvement defined in claim 1 wherein the hydrogenation of the 3,4-di-R-benzyl-cyanide is effected on a Raney-nickel catalyst washed with a 3% aqueous ammonium carbonate solution.

4. The improvement defined in claim 1 wherein dehydrogenation of the base of the isoquinoline derivative obtained by cyclization of the N-(3',4'-di-R-phenyl-acetyl)-3,4-di-R-phenyl-ethylamine is effected in the presence of at most 10% by weight of a Raney-nickel catalyst, calculated on the cyclic isoquinoline base.

* * * * *